United States Patent [19]

Sakamoto et al.

[11] Patent Number: 4,927,531
[45] Date of Patent: May 22, 1990

[54] AN AXIALLY ADJUSTABLE-TYPE COLUMN DEVICE

[75] Inventors: Kiyoaki Sakamoto, Hofu; Kenichi Matsubara, Shinnanyo; Yasuhiro Nakahara, Yamaguchi; Masaki Nomura, Tokuyama, all of Japan

[73] Assignee: Tosoh Corporation, Shinnanyo, Japan

[21] Appl. No.: 315,857

[22] Filed: Feb. 27, 1989

[30] Foreign Application Priority Data

Feb. 25, 1988 [JP] Japan ................................. 63-43003

[51] Int. Cl.⁵ .......................................... B01D 15/08
[52] U.S. Cl. .................... 210/198.2; 210/656; 55/386
[58] Field of Search ..................... 210/635, 656, 198.2; 55/386; 422/70

[56] References Cited

U.S. PATENT DOCUMENTS

| 3,487,938 | 1/1970 | Patterson | 210/198.2 |
| 3,510,271 | 5/1970 | Emneus | 210/198.2 |
| 3,826,373 | 7/1974 | Andreotti | 210/198.2 |
| 3,966,609 | 6/1976 | Godbille | 210/198.2 |
| 4,350,595 | 9/1982 | Gunkel | 210/198.2 |
| 4,361,482 | 11/1982 | Teetz | 210/198.2 |
| 4,549,584 | 10/1985 | Morin | 210/198.2 |
| 4,597,866 | 7/1986 | Couillard | 210/198.2 |
| 4,627,918 | 12/1986 | Saxena | 210/198.2 |
| 4,636,315 | 1/1987 | Allen | 210/198.2 |
| 4,737,292 | 4/1988 | Ritacco | 55/386 |
| 4,752,391 | 6/1988 | Porsch | 210/198.2 |
| 4,769,141 | 9/1988 | Couillard | 210/198.2 |
| 4,797,209 | 1/1989 | Jackson | 210/198.2 |

FOREIGN PATENT DOCUMENTS

| 248379 | 12/1987 | European Pat. Off. | 210/198.2 |
| 61-61346 | 12/1986 | Japan | 210/198.2 |
| 623380 | 1/1987 | Japan | 210/198.2 |

OTHER PUBLICATIONS

Snyder, Introduction to Modern Liquid Chromatography Second Edition, John Wiley & Son Inc. 1979, pp. 92–100.

Primary Examiner—Ernest G. Therkorn
Attorney, Agent, or Firm—Oblon, Spivak, McClelland, Maier & Neustadt

[57] ABSTRACT

To form a gel bed in a cylindrical column for liquid chromatography, a gel bed section is provided between upper and lower liquid-tight partition members, positioned apart from each other at upper and lower positions in the column. Liquid is continuously percolated downward through the gel bed section to form a gel bed in the gel bed section and a liquid pressure is applied onto the upper partition to move the partition member downward following a downward movement of the upper surface of the gel bed.

2 Claims, 9 Drawing Sheets

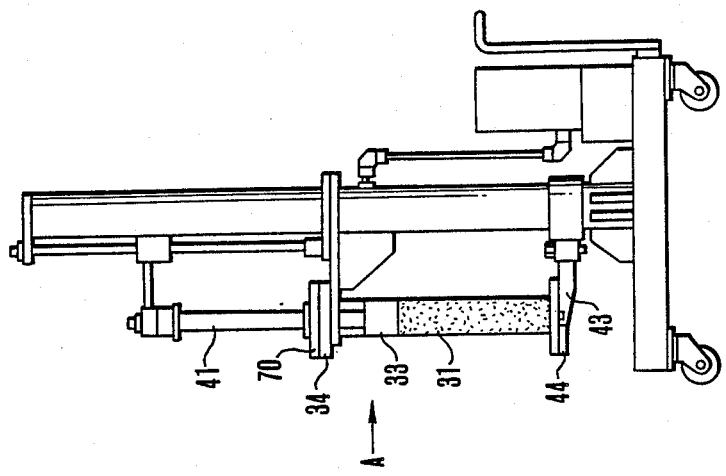
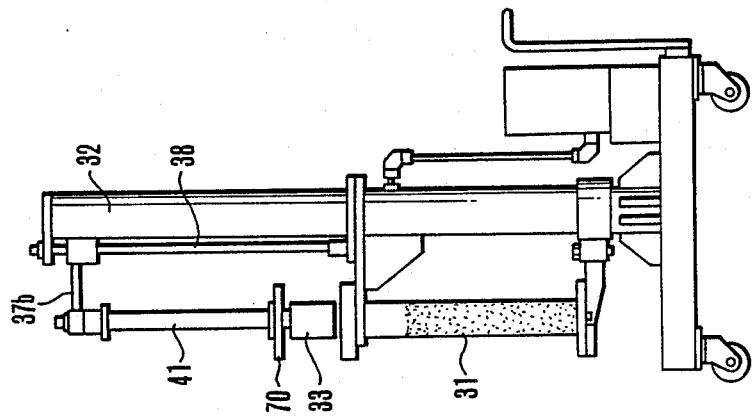
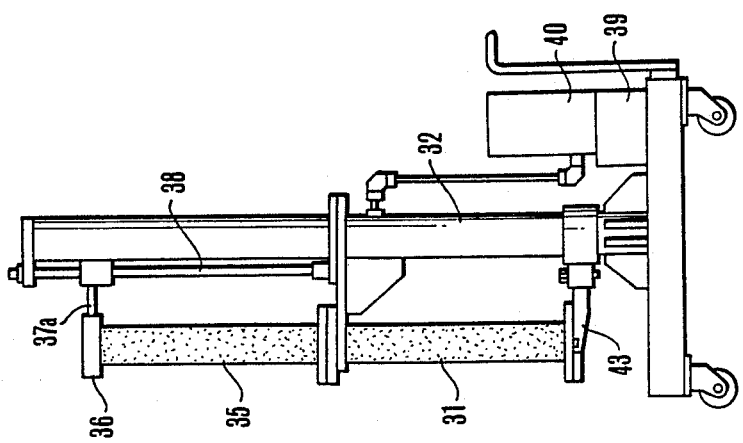

ANAXIALLY ADJUSTABLE-TYPE COLUMN DEVICE

BACKGROUND OF THE INVENTION

1. Field of the Invention:

This invention relates to a column structure of liquid chromatography used for separating and purifying materials and a method of high-performance packing of gels into this column.

2. Discussion of the Background:

In conventional liquid chromatographic devices, a column wherein slurry dispersed with gel is packed by liquid-flow is generally used for the column as the main component for separation and purification.

This method of packing the gels by liquid-flow is called a slurry packing method and is generally operated as shown in FIGS. 5(a) through 5(e). A reservoir 4 is connected to the upper end of a column body 1 having a lower flange 2 blocking the bottom thereof. A homogeneous gel slurry 5 of predetermined quantity and density is poured into the reservoir from above (see FIG. 5(a)). Then, an upper flange 3 is attached to the upper end of the reservoir 4. And a gel bed 6 is formed within the column body 1 by liquid-flow through the column body and reservoir and pressurization with a high pressure pump (see the top and bottom openings for liquid flow and for pressurization, shown only in FIG. 5(b)). After the liquid-flow and pressurization, supernatant liquid in the reservoir 4 is discharged by a pump and the like (see FIG. 5(c)), and the reservoir 4 is removed from the column body 1. The gel bed 6 heaps up over the top of the column body 1 when the reservoir 4 is removed therefrom (see FIG. 5(d)).

After the heap of the bed is removed, the upper flange 3 is fixed to the top of the column body 1 to finish the packing operation (see FIG. 5(e)).

This slurry packing method has been practiced as one of most common and superior packing methods because the advantages that stable gel beds and remarkably increased performance of the column can be obtained.

However, in conjunction with recent developments in biotechnology and its increasing importance to studies in related fields of biochemistry, many kinds of gels for liquid chromatography have been in development. It has been desired that the users can themselves easily pack and replace these gels into a column which is most suitable for the objective ingredients and matching size (diameter and length) for a required quantity to be treated.

In order to so form stable gel beds in a column for separation and purification or to fill, as another object, a void in the top of liquid inlet due to the volume change of the gel bed during the liquid chromatographic operation, a method to move a liquid dispersing plate and a liquid collecting plate situated at the upper and lower ends of the inside of the column has been proposed. A device utilizing this method to move a liquid dispersing plate (or a liquid collecting plate) may be classified as an axially adjustable-type column for preparative liquid chromatography interconnected with a pneumatic, hydraulic, or mechanical driving mechanism for compressing and pressurizing gel beds and the method may be called a pressurized packing method.

An example utilizing such a pressurized packing method as disclosed in Japanese Patent Publication No. Sho 58-20284 is shown in FIG. 6. In FIG. 6, a piston-like sliding body 8 having a head 9 is fit liquid-tightly and vertically movably in the column body 10. The liquid collecting plate 13 is attached to the upper end of the above mentioned head 9. While the sliding body is at the lower dead point of its travelling path, homogeneous gel slurry 11 is poured into the column body 10. After that, the liquid dispersing plate 16 and a cover 12 are fixed to a fixing flange 14 on top of the column body.

When the sliding body 8 is moved upward from its lower dead point by a drive shaft 15, for example by utilizing a pneumatic or hydraulic jack, pressure is applied to the homogeneous gel slurry 11 to form the gel bed. Removal of the gel bed for replacement is performed by lifting the sliding body 8 with the cover 12 removed. Then it is ready for the next chromatographic operation.

FIG. 7 shows another example of the pressurized packing method as disclosed in Japanese Laid-Open Patent Application No. Sho 61-28864. A column for liquid chromatography 23 is fixedly attached to a column pedestal 24. After the homogeneous gel slurry is poured through the top of the column 23, an adjustable plug (not shown) is attached to the top of the inside of the column. A shaft 22 connected with this adjustable plug is extended upward out of the column. The upper end thereof is fixed to an adjustable plug transfer pedestal 21. Under this condition, threaded rotation shafts 18 are rotated, via the reducing mechanism 19, by the rotation of a motor 20. Since rotation shafts 18 are threaded in the transfer pedestal 21, they cause the pedestal to move vertically. A gel bed is formed by lowering the adjustable plug transfer pedestal 21 and the adjustable plug at a fixed rate to apply pressure to the homogeneous gel slurry in the column 23 and by discharging only the liquid to the outside through piping on both sides of the column (not shown). When the gel in the column is no longer usable, the lower flange 17 is removed, the adjustable plug transfer pedestal 21 is lowered, and the gel is discharged from the bottom of the column 23 to prepare the column for the subsequent packing.

Though quite different from the above method which applies pressure for the formation of a gel bed, a column of such a structure that an adjustable plug is built therein has also been proposed for packing by pressure the void at the liquid inlet in the column, which void occurs due to the volume change of the gel bed during the liquid chromatographic operation. An example is disclosed in Japanese Utility Model Publication No. Sho 43-22959, and shown in FIG. 8. In the figure, if the top of the gel bed 25 is lowered in the course of time due to the inflow of liquid through a treating liquid inflow passage 29, pressurized gas is supplied into a pressurized gas chamber 27 through a flow-in duct 26 and an adjustable body 28 always applies pressure on the gel bed 25 and moves downward as required. Therefore, the void is not formed during that time. Element 30 is a seal ring for sealing air and liquid.

In an axially adjustable column for separation and purification according to the conventional pressurized packing method, a special mechanism is required to constantly maintain the travel speed of the adjustable plug by a pneumatic, hydraulic or mechanical driving mechanism and to provide a large overload for pressurizing the gel bed as in the cases of Japanese Patent Publication No. Sho 58-20284 or Japanese Laid-Open Patent Application No. Sho 61-28864, described above, in order to move either one or both of the liquid dispersing plate and the liquid collecting plate. In order to meet with these requirements, the pneumatic, hydraulic or mechanical driving mechanism will inevitably be structured in large scale.

Moreover, such a mechanical driving mechanism forms a gel bed by pressing it with a strong force, and accordingly the density distribution of the gel bed is liable to become uneven in the axial direction, and it is difficult to achieve a high column performance as has been attained by conventional slurry packing methods.

The method described in Japanese Utility Model Publication No. Sho 43-22959 has as its object to fill the void which arises between the gel bed and the adjustable plug during liquid chromatographic operation, and has no object to form the gel bed. Further this method seems to provide no effective method for forming the bed. For instance, even if this method of moving the adjustable plug with use of pressurized gases is applied to the gel bed formation, the transfer speed of the adjustable plug cannot be controlled at a fixed rate due to the cushion effect of the pressurized gas, and desired separation performance cannot be constantly accomplished. And when leakage happens to occur at the sealing surface between the adjustable plug and the inner wall of the column, a problem arises that separation performance of the column will be decreased drastically due to the flow of the pressurized gases through the gel bed.

As has been described above, in contrast to the slurry packing method wherein high column performance is achieved, it is difficult to form a satisfactory gel bed by any of the conventional pressure packing methods described in Japanese Patent Publication No. Sho 58-20284 and Japanese Laid-Open Patent Application No. Sho 61-28864, or the method of Japanese Utility Model Publication No. Sho 43-22959 utilizing the similar axially adjustable-type column.

It may be said that the features of the conventional slurry packing method for obtaining high performance and those of the pressurized packing method for rapidly forming the gel bed effectively by applying pressure on the adjustable plug are mutually exclusive.

SUMMARY OF THE INVENTION

An object of the present invention is to solve these problems by achieving the performance of the conventional packing method with the convenience of the pressure packing method.

Another object of the present invention is to provide an axially adjustable-type column having a structure capable of performing a slurry packing method and provide a packing method utilizing this column.

More specifically, the present invention provides a method to form the gel bed in a cylindrical column for liquid chromatography, in which the gel bed section within the cylindrical column is installed between upper and lower liquid tight partition members located apart from each other in the column, and a gel bed is formed by continuously percolating a downward liquid-flow through the gel bed disposed between the upper and lower partition members, and applying liquid pressure on the upper partition member which serves as an adjustable plate during the percolating step, so as to move downward the upper partition member in response to the downward movement of the upper surface of the gel bed.

Further, the present invention provides a column device for forming the gel bed therein having a cylindrical column into which the gel is packed, a pair of upper and lower partition members to form a gel bed section therebetween and to liquid-tightly seal the gel bed section, with at least one of the pair of partition members being provided with a flow path therethrough to flow the liquid in one of upward and downward directions through the gel bed section, a pressure balance chamber to which the upper surface of the upper partition member is exposed, and pressure supply means for transferring liquid pressure of the liquid flowing through the flow path to the pressure balance chamber Particularly, the column device can be provided as an extremely simple structure by sharing the liquid pressure to be supplied to the pressure balance chamber with the supply source supplying the liquid to the gel bed section.

The present invention has an advantage that a constant flow pump, for instance, may be used to supply liquid for forming the gel bed in the column the pump and for chromatographic operation. The axially adjustable-type column device according to this invention has advantages that a special mechanical driving mechanism used in the pressurized packing method is not required for forming the gel bed as it is formed by the slurry packing method using liquid-flow, and moreover, as the liquid-flow to form the gel bed is provided by the constant flow pump, a special adjusting mechanism is not required for pressurizing and forming the gel bed with a constant flow rate and pressure.

BRIEF DESCRIPTION OF THE DRAWINGS

A more complete appreciation of the invention and many of the attendant advantage thereof will be readily obtained as the same becomes better understood by reference to the following detailed description when considered in connection with the accompanying drawings, wherein:

FIGS. 2(a), 2(b) and 2(c) are schematic views showing an example of an axially adjustable column device for the liquid chromatography and packing operations;

DETAILED DESCRIPTION OF THE PREFERRED EMBODIMENT

Figure 1A:
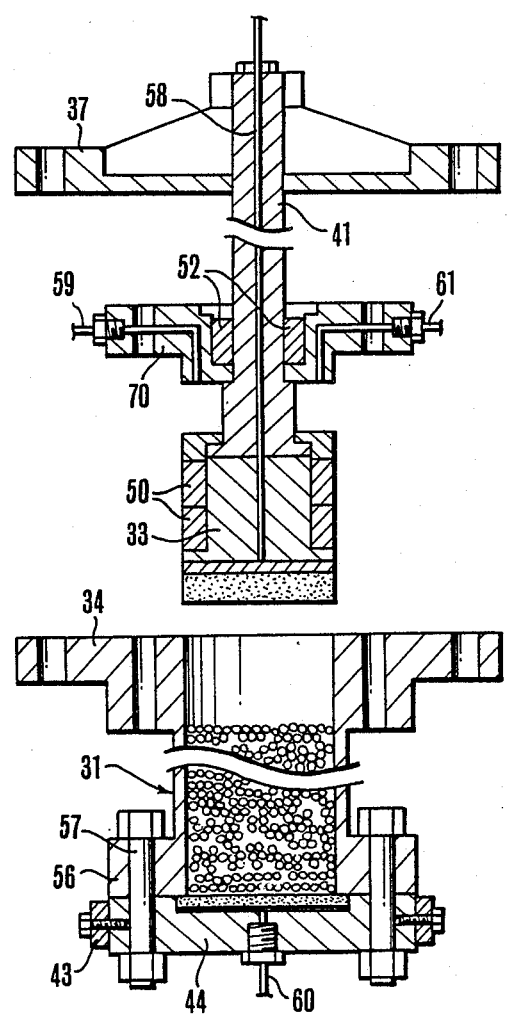
Figs. 1(a) and 1(b) show cross-sectional structural views of an axially adjustable column according to this invention.

Now, the structure and operation method of this device will be explained by way of an embodiment with reference to the accompanying drawings, but the present invention is not limited to the embodiment.

A brief operational procedure will be explained first with reference to FIGS. 2(a)–2(c).

FIGS. 2(a)–2(c) schematically show the axially adjustable-type column device for liquid chromatography according to the present invention and the packing procedure thereof. FIG. 2(a) shows the state when the homogeneous gel slurry is poured, wherein a reservoir for packing 35 is set on an axially adjustable-type column body 31 (hereinafter called a "column body") fixedly attached to a column support pole 32. A cylindrical body of stainless steel is preferably adopted for the column body 31, generally in consideration of corrosion resistance, chemical resistance, workability, and structural strength, but is not limited thereto. A reservoir cap 36 is supported by an adjustable plug transfer pedestal 37a through which the cap is moved vertically by a hydraulic cylinder (not shown) built in the column support pole 32. A slide rod 38 acts as a guide for the vertical movement of the transfer pedestal. A valve unit 39 is provided with a selector valve or the like to form a predetermined flow path for packing operations or liquid chromatographic operations. A pneumatic-hydraulic converter 40 for the cylinder operation described above actuates the transfer pedestal 37a described above, and the switching operations of the selector valve of the valve unit 39 described above and the vertical transfer operation of the adjustable plug transfer pedestal 37a and so on are automatically controlled by a controller which is not shown. By the way, the transfer pedestal 37a described above is rotatable around the slide rod 38 on a level plane, which forces an adjustable plug unit which will be described later to rotate into alignment with the column body 31 when a gel bed is formed.

In the packing operation, the homogeneous gel slurry which has been adjusted in concentration is introduced into the reservoir for packing 35 and the column body 31 which are set as shown in FIG. 2(a) and is left until the gel spontaneously sinks. The leftover supernatant in the reservoir 35 is then discharged and the reservoir 35 is removed. The length of the reservoir 35 to be used depends on the density of the preset gel slurry and the height of the required gel bed. Therefore, in some cases the packing can be started after the gel slurry is directly introduced into the column body 31, without using the reservoir 35, either immediately or after having been left to sink spontaneously.

Then the gel bed is formed by the slurry which has been packed as described below.

FIG. 2(b) shows the state wherein the transfer pedestal 37a is rotated around the slide rod 38 on a level plane to position the adjustable plug unit (33, 41, 70) in alignment above the column body. In the Figure, 33 is the adjustable plug, 41 an adjustable plug rod supporting the adjustable plug 33 at the lower end and having an inside liquid-flow path communicating to the end of the adjustable plug 33, and 70 is an upper flange arranged to seal the column body. The adjustable plug unit which consists of the parts mentioned above is supported by the adjustable plug transfer pedestal 37b which is vertically movable along the slide rod 38 supported by the column support pole 32 and, as described above, is positioned from an offset position shown in FIG. 2(a) to the alignment position above the column body 31 by the rotation of the adjustable plug transfer pedestal 37b around the slide rod 38.

FIG. 2(c) shows the device when operating to form the gel bed from the sedimentation which has sunk spontaneously during the state shown in FIG. 2(a). The adjustable plug unit described above moves downward from the state shown in FIG. 2(b) to insert the adjustable plug 33 into the column body 31 until the upper flange 70 is fixedly set onto the upper flange 34 of the column. Thereby, a pressure balance chamber 51 (FIG. 1(b)) is formed as an open space between the adjustable plug 33 and the upper flange 70.

Now, the operation for forming the gel bed (hereinafter called "a bed forming") is performed by flowing liquid by a constant flow pump, and an explanation of the operation will be given in detail with reference to FIGS. 1(a) and 1(b).

Figure 1B:
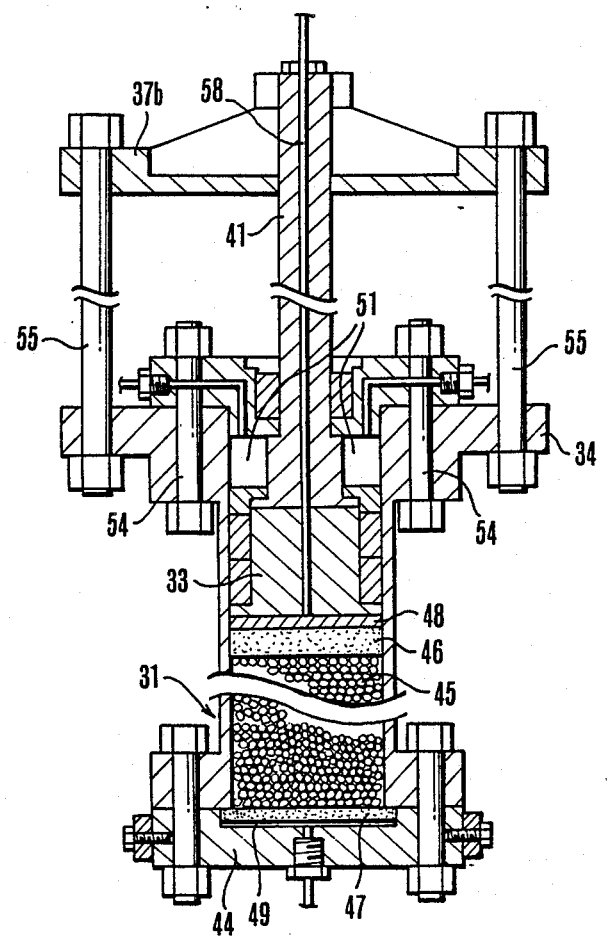

FIGS. 1(a) and 1(b) shows cross-sectional views of the column body 31 taken in the direction of the arrow A of FIG. 2(c);, FIG. 1(a) illustrates the adjustable plug 33 when ready to be inserted into the column body 31 (that is, at a position corresponding to FIG. 2(b)), and FIG. 1(b) illustrates the adjustable plug 33 when inserted (that is, at a position corresponding to FIG. 2(c)). Moreover, all the parts of the device of this embodiment which are brought into contact with the liquid should preferably be composed of stainless steel (SS316) in consideration of the required resistance to chemical agents and the like, but are not so limited, depending on the nature of the liquid to be used.

The inside of the column body is composed of the gel bed 45. The perforate liquid dispersing plate 46 is situated at the upper end of the bed 45 in case where the liquid flow direction is downward, and the perforate liquid collecting plate 47 is situated at the lower end. When the liquid-flow direction is made to be upward, the positional relation between the liquid dispersing plate and the liquid collecting plate described above is reversed. These plates also prevent the gel particles from leaking out of the column.

For the liquid dispersing plate 46 and the liquid collecting plate 47 mentioned above, stainless steel sintered porous plates are generally used and in this embodiment, together with the supporters 48 and 49 holding them; one of these plates is attached to the lower part of the adjustable plug 33 and the other to the upper part of the lower flange 44. Furthermore, supporters 48 and 49 should favorably function to rectify the flow of the liquid, i.e., to prevent backflow.

A seal rings 50 are fitted in a circumferential groove of the adjustable plug 33 to prevent the liquid and gel in the column and the pressure balance chamber 51 from leaking. A seal ring 52 prevents the liquid in the pressure balance chamber 51 from leaking out of the column when the adjustable plug rod 41 is sliding. V-packing rings of polytetrafluoroethylene (PTFE) and the like are favorably used for these seal rings.

The upper flange 70, together with the adjustable plug 33, is detachable from the column body 31 and may tightly fastened to the upper flange 34 with bolts and nuts 54 when the adjustable plug 33 is inserted into the column body 31. The adjustable plug transfer pedestal 37b fastened to the upper end of the adjustable plug rod 41 and the upper flange 34 of the column are connected via locking means in the form of bolts and nuts 55 after the bed forming operation, thus preventing the adjustable plug 33 from moving upward during the liquid chromatography operation.

Now preparations are completed for preparation of the liquid chromatographic processing.

When the above mentioned device is used for liquid chromatographic processing and the replacement of the gels is required due to the deterioration of the performance or due to contamination, the gels must be discharged from the column body 31. In the device according to this embodiment, the bolts and nuts 57 connecting the lower flange 56 of the column and the lower flange 44 are first removed. The lower flange holder 43 extending from the column support pole 32 (see FIG. 2(c)) and holding the lower flange 44 between its U-shaped arms is then rotated on a level plane around the column support pole to remove the lower flange 44 from the shaft of the column body 31. After that, the gels can be easily discharged downward by liquid-flow through a pipe line 58 by use of the constant flow pump. A receiver for extracted gels (not shown) should be placed below the column body 31.

The structural arrangements described above, including the arrangements for discharging the used gels, are also features of the present invention.

In the axially adjustable-type column of the above structure, the adjustable plug 33 equipped with the liquid dispersing plate (or a liquid collecting plate), is moved downward when the bed is formed by the liquid-flow introduced through the pipe line 58 in conjunction with the downward movement of the upper surface of the bed.

Generally, as has been described in the explanation of the related art, fine adjustment of the speed is difficult for movement driven by pneumatic or hydraulic forces. In a mechanical driving system, large scale equipment is required to reduce the rotation speed of the motor by a worm gear or the like.

Contrary to the above, this invention has an advantage that the liquid feed from the constant flow pump to the pipe line 58 is branched into a liquid feed pipe line 59, and the slurry packing is attained by the liquid-flow and a rapid bed formation is achieved by moving the adjustable plug 33 in response to movement of the upper surface of the gel bed 45.

That is to say, when the formation of the gel bed 45 is performed by the liquid-flow from the pipe line 58, an opposing force to push the adjustable plug upward is exerted. It is not easy to move the adjustable plug 33 so as to follow the movement of the upper surface of the bed at a fixed rate by pneumatic, hydraulic mechanical driving means against the opposing force which changes with time during the packing operations. In this embodiment, the adjustable plug 33 is moved in proportion to the quantity of pressurized liquid supplied into the pressure balance chamber 51 through the liquid feed pipe line 59.

The total volume of pumped liquid equals the volume of the liquid fed to the liquid feed pipe line 59, and that fed-through pipe line 58, which is discharged from the pipe line 60; that is, the slurry packing is made possible by a constant liquid feeding volume. Further, the liquid feeding to the liquid feed pipe line 59 and the pipe line 58 may be made by two separate pumps, or a shut-off valve may be attached in the midway between the lines of the pipe line 58 and the liquid feed pipe line 59. By controlling them, it is possible that the slurry packing and the movement of the adjustable plug 33 accompanying the upper surface of the gel bed 45 are performed simultaneously or the operation for moving the adjustable plug 33 is performed only after the gel bed 45 has been formed. Meanwhile it is necessary to open the exhaust pipe line 61 to exhaust air from the pressure balance chamber 51 and to close the exhaust pipe line 61 when the packing is performed.

The degree of the liquid pressure applied to the pressure balance chamber 51 described above should be basically determined by the relation between the downward liquid pressure working on the adjustable plug 33 (that is, the liquid pressure from the pressure balance chamber) and the upward liquid pressure (that is, the liquid pressure from the formed portion of the gel bed), but the latter may decrease considerably when the liquid is discharged from the lower pipe line 60. Accordingly, required functions and performances are satisfactorily achieved by the liquid supply from the same supply source even with the adjustable plug 33 having differences between the upper and lower pressures applied to the surfaces as explained in the above FIG. 1.

Also, there is an extremely great difference between the liquid pressure required for moving the adjustable plug 33 downward following the downward movement of the upper surface of the gel bed and the liquid pressure required for the packing method explained in the conventional methods. Accordingly, strict controls on the setting of the pressure for the pressure balance chamber 51 are not specially required in this invention. And generally, it is particularly preferable that the supply source for flowing the liquids to form the gel bed is shared with the pressure balance chamber as described above, from the points of view of limiting the required equipment making the whole system smaller in size, lowering the production cost and other factors.

After the completion of the bed formation, the bolt and nut 55 and the adjustable plug transfer pedestal 37b, hence the adjustable plug 33, are fixed to the upper flange of the column of the column body 31. Then, this device as arranged above is used for liquid chromatography.

Figure 3:
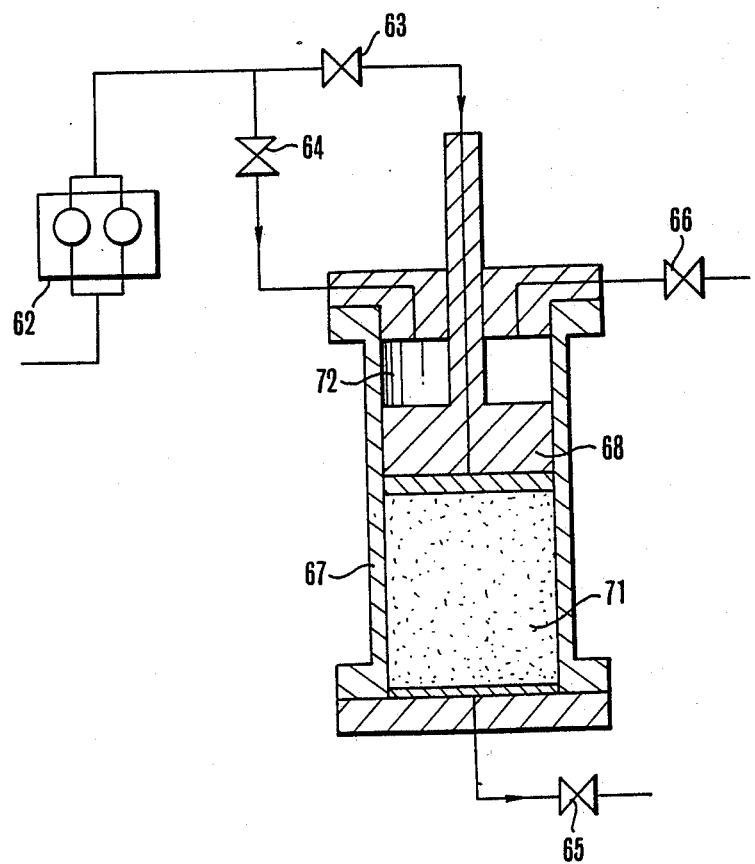
FIG. 3 shows the liquid-flow of the packing operation.

FIG. 3 schematically shows the liquid-flow when the gel bed is formed. In this figure, the packing solvent from the constant flow pump 62 is branched midway to flow through a valve 63 on the adjustable plug side and a valve 64 on the pressure balance chamber side to form the gel bed 71 and to move the adjustable plug 68 downward. The discharge of the packing solvent from the column body 67 is performed through the drain valve 65, and after the exhaust of the pressure balance chamber 72 is finished, the exhaust valve 66 is closed.

In this way, by use of only the constant flow pump (this same constant flow pump can be used for the liquid chromatography), it is possible to perform the slurry packing method for preparing a high performance column by liquid-flow without using any specific driving mechanism and to speed up the packing operations by utilizing the features of the axially adjustable-type column.

When the column in which has been completed the bed formation is used as a separation system in liquid chromatography, the supply of the eluent can be made through the pipe lines 58 or 60 in FIG. 1. In either case, the sample supply is made on the supply side of the eluent, and the output liquid of the constant flow pump used for the packing operation is introduced into the pipe lines 58 or 60 to keep the liquid chromatography system compact.

EXAMPLE 1

Tests were made on individual column performances obtained by the packing method according to this invention, and the conventional slurry packing method and mechanical pressure packing method, using the gel (TSKgel ODS-120T, Tosoh Corporation) for reversed-phase chromatography in which separations are made based on the partition and absorption utilizing the difference in polarity. The results of the tests will be explained as the example and the comparison.

As for the pressure packing method in the comparative example, the test was performed by compressing the gel bed with a strengthened function of the hydraulic mechanism explained in FIG. 2 and moving the adjustable plug utilizing the driving mechanism thereof.

By utilizing the axially adjustable-type column device of 10 cm inner diameter according to this invention, the gel was sunk in the state of FIG. 2(b), and then the reservoir was removed, the adjustable plug was attached, and the packing was performed at a liquid-flow rate of 3 l/min, under a pressure of 100 kg/cm2G. The time required for the packing was approximately 30 minutes and the height of the gel bed was 60 cm.

Figure 4:
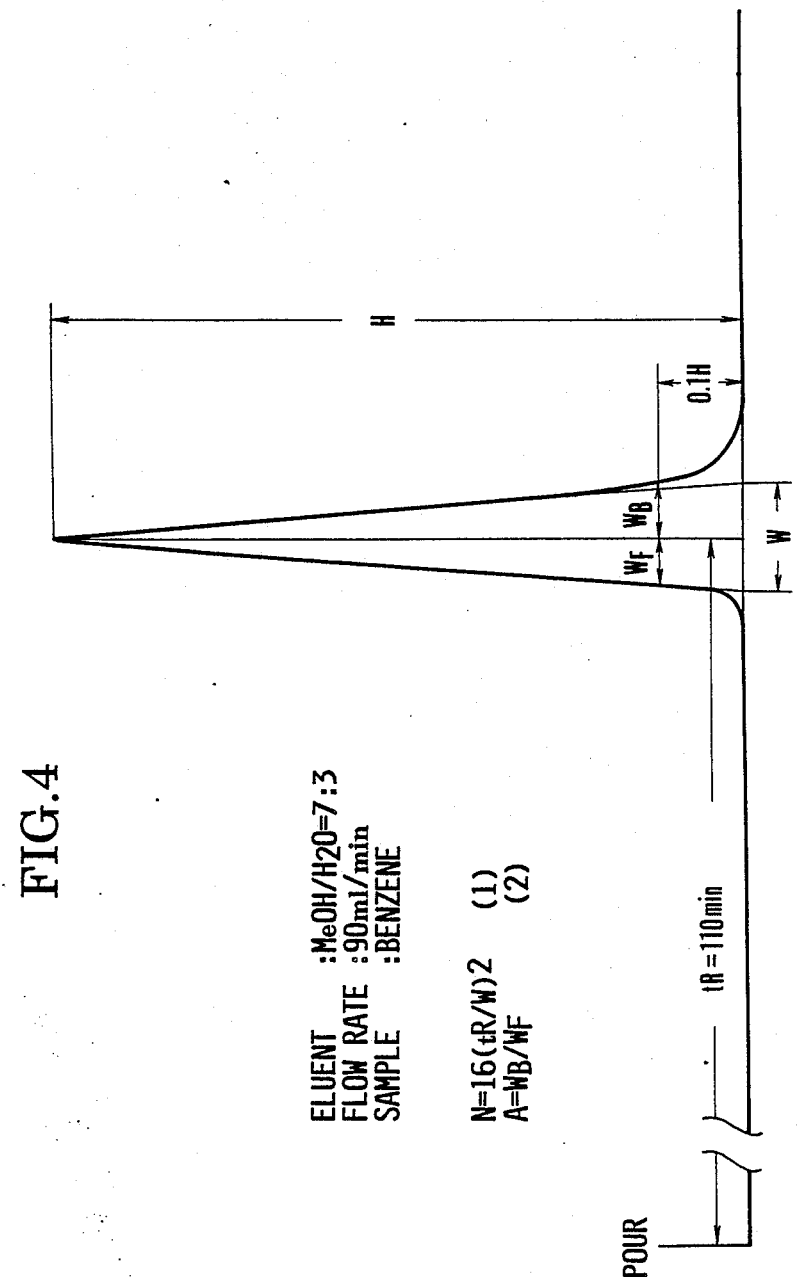
FIG. 4 schematically shows a method of the calculation of column performance when a column packed according to this invention and a column packed by a conventional method are used as columns for liquid chromatography.
Figure 5:
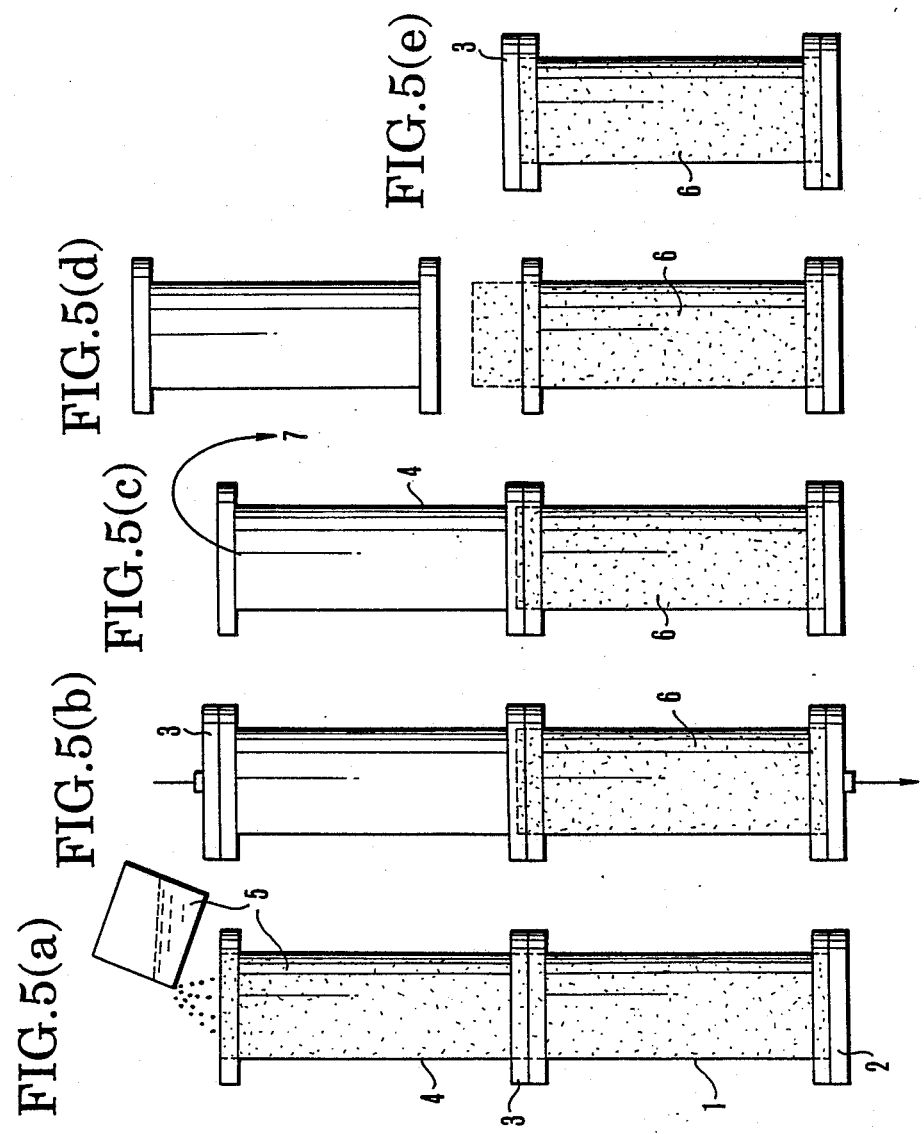
FIGS. 5(a)–5(e) schematically illustrate a conventional packing method.
Figure 6:
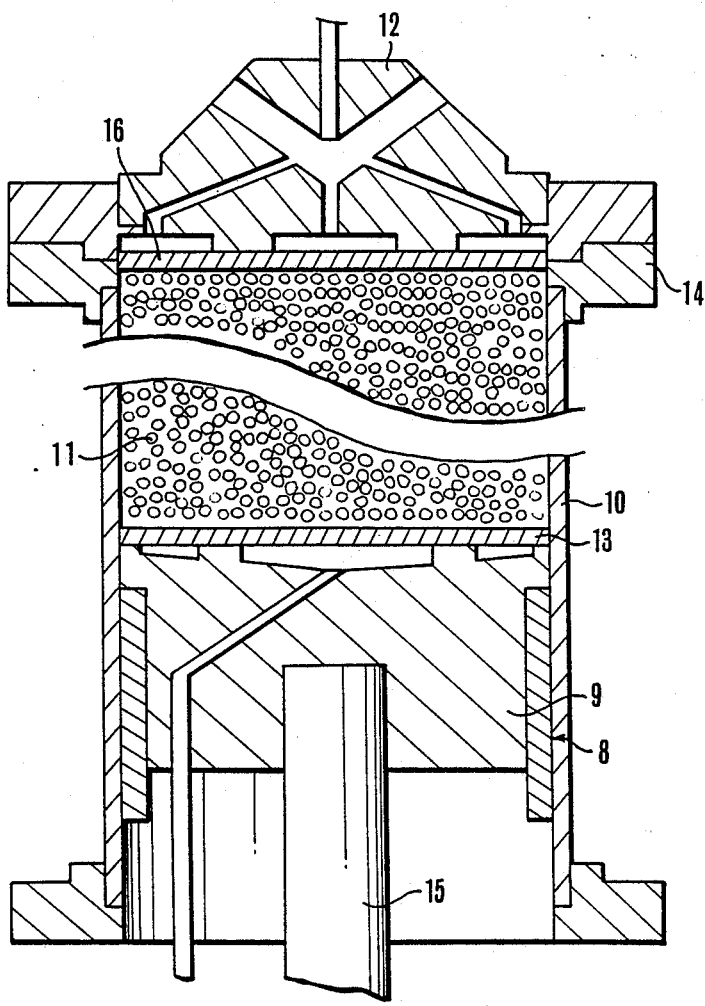
FIG. 6, FIG. 7 and FIG. 8 respectively show examples of conventional axially adjustable-type columns.
Figure 7:
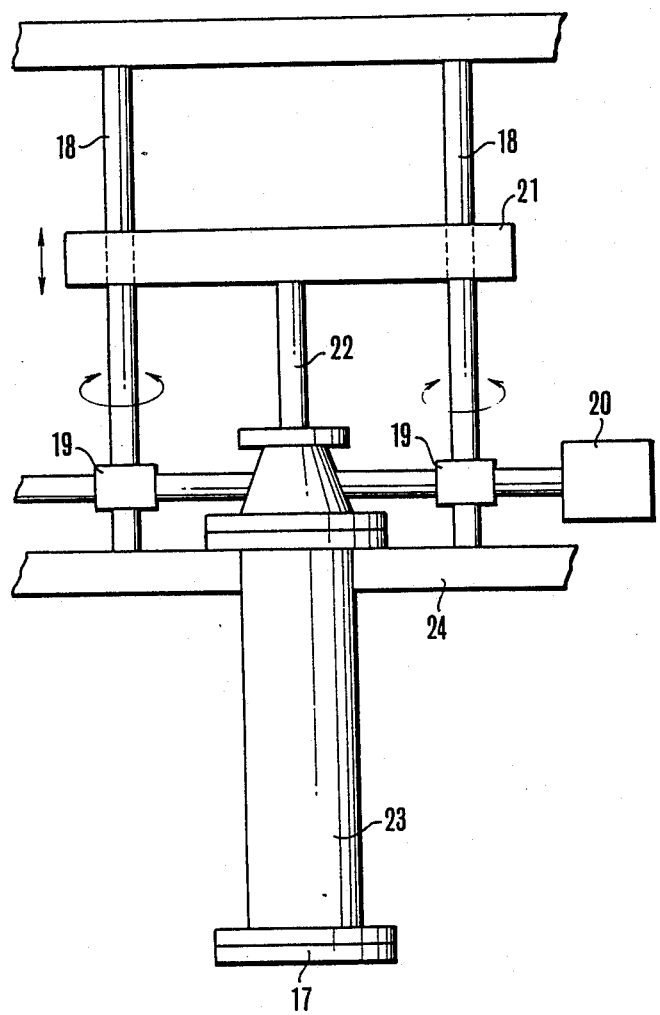
Figure 8:
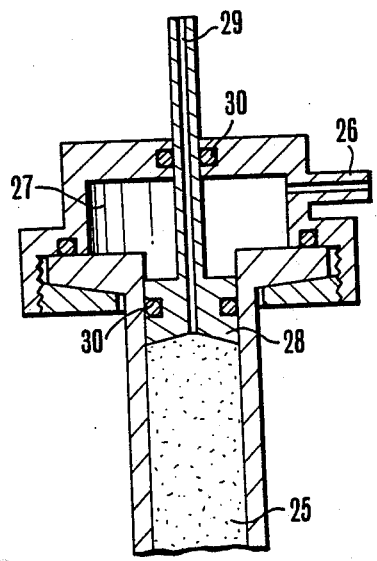

FIG. 4 shows the results of tests using the benzene elution as a sample with the use of this column. Theoretical plate numbers N and asymmetry factors A are generally used as the indexes for evaluating the column performances. They are determined from the formulae (1) and (2) respectively shown in FIG. 4.

The results of the performance evaluation of the packed column in this example formed by the packing method according to this invention was 16000 plates for the theoretical plate number and approximately 1.14 for the asymmetry factor as shown in Table 1.

TABLE 1

| Packing method | Theoretical plate No. | Asymmetry factor |
| --- | --- | --- |
| Packing method by this invention | 16200 | 1.13 |
|  | 15800 | 1.14 |
|  | 16000 | 1.14 |
|  | 15500 | 1.14 |
|  | 16400 | 1.13 |
| Conventional packing method | 15600 | 1.14 |
|  | 16100 | 1.13 |
|  | 15000 | 1.15 |
|  | 16800 | 1.12 |
|  | 17500 | 1.12 |
| Mechanical pressure packing method | 9700 | 1.46 |
|  | 11700 | 1.33 |
|  | 12800 | 1.29 |
|  | 9800 | 1.46 |
|  | 10500 | 1.41 |

Under the same conditions, using the column of 60 cm in length, the results of the performance evaluation tests on the packed column formed by the conventional slurry packing method showed nearly the same results compared with that of the above mentioned system of the invention (see Table 1).

However, in the case of the conventional slurry packing method, operations for separating the reservoir and attaching the upper flange are required and much attention had to be p id for strictly controlling them and maintaining the fastening force of the upper flange constant at a fixed rate.

One advantage of the packing operation according to this invention is that need for the attention described above is not required. As understood from the results of Table 1, a desirable tendency is recognized in that irregularity of the performance of the packed column by the packing method according to this invention is smaller than that by the conventional slurry packing method. It is supposed that the operation with good reproducibility is caused by the above described features.

The same lot gel was also packed by the above described mechanical pressure packing method at a hydraulic compression pressure of 100 kg/cm2G. The results of the performance evaluation tests on the column of the effective gel bed height of 60 cm and 10 cm inner diameter under the same conditions obtained by this pressurized packing method are also listed in Table 1. As can be seen from the table, it is clear that the performance of the packing method has been effectively improved according to this invention.

The advantages of this invention are that the packing method and the adjustable plug column device according to this invention can offer an axially adjustable column system enabling easy packing operations for liquid chromatography for separation and purification without losing high column performance of the conventional slurry packing method.

Obviously, numerous modifications and variations of the present invention are possible in light of the above teachings. It is therefore to be understood that within the scope of the appended claims, the invention may be practiced otherwise than as specifically describe herein.

What is claimed as new and desired to be secured by letters patent of the United States is:

1. An axially adjustable-type column device used for liquid chromatography, comprising:
   a cylindrical column to be packed with gel;
   a pair of upper and lower partition members for forming a gel bed section therebetween and for liquid-tightly sealing said gel bed section, with at least one of said pair of partition members being provided with means for forming a flow path therethrough to flow a liquid in one of upward and downward directions through the gel bed section;
   a pressure balance chamber to which the upper surface of the upper partition member is exposed;
   pressure supply means including a constant flow pump for transferring a liquid pressure of the liquid flowing through the flow path to the pressure balance chamber, whereby said upper partition member is pressed toward the gel bed section; and
   means for locking the position of said upper partition members, whereby said upper partition member may be pressed onto the gel in said cylindrical column by fluid pressure in said pressure balance chamber during a column packing operation and whereby said upper partition member may be locked in place during a separation operation.

2. An axially adjustable-type column device for liquid chromatography, comprising:
   a cylindrical column to be packed with a gel;
   a lower partition member in said column;
   an upper partition member connected to a plug movably fittable in said column above said lower partition member to form a fluid tight gel bed section therebetween;
   liquid supply means for supplying a pressurized liquid to said gel bed section through one of said lower and upper partition members and for permitting a discharge of the liquid from said gel bed section through the other of said lower and upper partition members;
   means for forming a pressure balance chamber above said plug;
   means including a constant flow pump for applying the pressure of the pressurized liquid to said pressure balance chamber, whereby the pressure in said pressure balance chamber varies as a function of the liquid flowing through said gel bed section so that said upper partition may move downwardly in response to a downward movement of an upper surface of a gel bed in said gel bed section during a column packing operation, and
   means for locking the position of said plug, whereby said upper partition member may be locked in place during a separation operation.

* * * * *